United States Patent
Barthelmes et al.

(10) Patent No.: US 12,246,413 B2
(45) Date of Patent: Mar. 11, 2025

(54) ASSEMBLY METHOD AND A SCREWDRIVING TOOL AND SCREW KIT

(71) Applicant: Aesculap AG, Tuttlingen (DE)

(72) Inventors: Sven Barthelmes, Emmingen-Liptingen (DE); Pedro Morales, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 18/554,258

(22) PCT Filed: Apr. 6, 2022

(86) PCT No.: PCT/EP2022/059090
§ 371 (c)(1),
(2) Date: Oct. 6, 2023

(87) PCT Pub. No.: WO2022/214535
PCT Pub. Date: Oct. 13, 2022

(65) Prior Publication Data
US 2024/0189967 A1 Jun. 13, 2024

(30) Foreign Application Priority Data
Apr. 8, 2021 (DE) .................... 10 2021 108 715.5

(51) Int. Cl.
*F16B 23/00* (2006.01)
*A61B 17/00* (2006.01)
(Continued)

(52) U.S. Cl.
CPC .......... *B25B 13/48* (2013.01); *A61B 17/2816* (2013.01); *F16B 23/0007* (2013.01); *A61B 2017/00526* (2013.01)

(58) Field of Classification Search
CPC ....... F16B 35/06; F16B 23/0007; B21K 1/463
See application file for complete search history.

(56) References Cited

U.S. PATENT DOCUMENTS 2,568,439 A * 9/1951 Friedman ............... B21K 1/463
470/205
3,945,071 A * 3/1976 Flodin .................... B21K 1/463
470/205
(Continued)

FOREIGN PATENT DOCUMENTS

DE 10041576 A1 3/2002
DE 69809500 T2 3/2003
(Continued)

OTHER PUBLICATIONS

English Translation of KR-101264391-B1 (Year: 2011).*
(Continued)

*Primary Examiner* — Jacob J Cigna
(74) *Attorney, Agent, or Firm* — Christopher A. Rothe; CM Law

(57) ABSTRACT

An assembly method, a screwdriving tool and a screw kit for screwing a screw into an internal thread of a medical instrument to connect two branches of the instrument to each other so that the branches are pivotable relative to each other. The method includes: impressing a punch geometry into a screw head of the screw by applying an axial compressive force to the screw by the screwdriving tool, and rotating the screwdriving tool relative to the instrument about a screw longitudinal axis to transmit a torque in a positively locking manner from the screwdriving tool to the screw via the impressed punch geometry and to screw the screw into the internal thread.

6 Claims, 2 Drawing Sheets

(51) Int. Cl.
*A61B 17/28* (2006.01)
*B25B 13/48* (2006.01)

(56) References Cited

U.S. PATENT DOCUMENTS

| | | | |
|---|---|---|---|
| 4,151,621 A * | 5/1979 | Simmons | B21K 1/463 |
| | | | 411/407 |
| 6,161,273 A | 12/2000 | Rivera et al. | |
| 9,962,759 B2 * | 5/2018 | Chen | F16B 23/003 |
| 10,493,519 B2 * | 12/2019 | Ross | F16B 23/003 |
| 11,549,544 B2 * | 1/2023 | Tsuzaki | F16B 23/0053 |
| 2005/0129486 A1 * | 6/2005 | Totsu | B25B 13/485 |
| | | | 411/402 |
| 2005/0135898 A1 | 6/2005 | Bell et al. | |
| 2007/0157736 A1 | 7/2007 | Kawano et al. | |

FOREIGN PATENT DOCUMENTS

| | | | |
|---|---|---|---|
| FR | 3032345 A1 | 8/2016 | |
| KR | 101264391 B1 * | 11/2011 | |
| WO | WO-2005047715 A1 * | 5/2005 | B25B 15/008 |

OTHER PUBLICATIONS

Search Report received in German Application No. 10 2021 108 715.5 dated Feb. 1, 2022, with translation, 11 pages.
Search Report received in International Application No. PCT/EP2022/059090 dated Jul. 5, 2022, with translation, 5 pages.
Written Opinion received in International Application No. PCT/EP2022/059090 dated Jul. 5, 2022, with translation, 9 pages.

* cited by examiner

ASSEMBLY METHOD AND A SCREWDRIVING TOOL AND SCREW KIT

CROSS-REFERENCE TO RELATED APPLICATIONS

This application is the United States national stage entry of International Application No. PCT/EP2022/059090, filed Apr. 6, 2022, and claims priority to German Application No. 10 2021 108 715.5, filed Apr. 8, 2021. The contents of International Application No. PCT/EP2022/059090 and German Application No. 10 2021 108 715.5 are incorporated by reference herein in their entireties.

FIELD

The present disclosure relates to an assembly method for screwing a screw into an internal thread of a medical instrument, using a screwdriving tool in order to connect two branches of the instrument to each other such that the two branches are pivotable relative to each other. In addition, the present disclosure relates to a screwdriving tool for performing such an assembly method and to a screw kit comprising such a screwdriving tool and a screw.

BACKGROUND

For screwing a screw into an internal thread, for example in order to connect two branches of a medical instrument firmly to each other or in particular so that they can move relative to each other, for example pivotably, it is necessary to apply a torque to the screw. This torque can be transmitted to the screw in a form-fitting and/or force-fitting (i.e. frictionally engaged) manner, in particular by a screwdriving tool. Such a method for screwing in a screw is known, for example, from DE 100 41 576 A1 or from US 2005/135 898 A1. Alternatively, the two branches of the instrument can be joined by riveting, as known for example from DE 698 09 500 T2.

When screwing in the screw, the torque transmitted to the screw by the screwdriving tool has to overcome a thread friction force acting between the screw and the internal thread.

For force-fit torque transmission, the screw is subjected to an axial pressure/an axial compression force by the screwdriving tool so that a surface friction force is created between the screwdriving tool and the screw, and a friction torque resulting from the surface friction force is transmitted to the screw when the screwdriving tool is rotated. If the friction torque between the screwdriving tool and the screw is smaller than the torque resulting from the thread friction force, the screwdriving tool slips and the screw is not screwed in. This can cause the screwdriving tool to slip and damage a surface of the screw or a component comprising an internal thread.

The higher the axial pressure applied to the screw by the screwdriving tool, the greater the surface friction force and the resulting friction torque that can be transmitted from the screwdriving tool to the screw. However, since the axial pressure applied to the screw also acts on the internal thread and the thread friction force therefore increases as the axial pressure increases, the axial pressure cannot simply be increased at will in order to increase the torque that can be transmitted from the screwdriving tool to the screw in a frictionally engaged manner.

SUMMARY

It is therefore the object of the present disclosure to provide a suitable assembly method with which a screw can be screwed in particularly easily and reliably. In addition, a screwdriving tool for performing the assembly method and a screw kit with a screwdriving tool and a screw are to be provided.

More specifically, the assembly method serves for screwing a screw into an internal thread of a medical instrument using a screwdriving tool to connect two branches of the instrument so that the two branches are pivotable to each other.

The assembly method has the following steps:
  imprinting a punch geometry into a preferably unprofiled screw head of the screw by applying an axial compression force to the screw using the screwdriving tool itself, and
  rotating of the screwdriving tool relative to the instrument about a longitudinal screw axis in order to transmit a torque (in particular for setting a tightening torque or a screw-in depth of the screw) from the screwdriving tool (frictionally engaged as well as) in a form-fitting manner via the imprinted punch geometry to the screw and to screw the screw into the internal thread.

Accordingly, the core of the disclosure is that the screw head has a preferably unprofiled, i.e. smooth, for example flat or curved, surface without form-fitting engagement surfaces prior to assembly. In particular, the screw head may be configured as a body of revolution, i.e., a rotationally symmetric body that maps onto itself when rotated through any angle. During assembly, the punch geometry is imprinted into the screw head, so that after assembly the screw head has a profiled, i.e. relief-like, surface in which a recess is configured in the form of the punch geometry, which can serve as a form-fitting engagement surface when the screw is screwed in. When the screwdriving tool is turned, the punch geometry of the screwdriving tool engages in the imprinted punch geometry so that the torque from the screwdriving tool to the screw is not only frictionally engaged (by the application of the axial compression force and the frictional torque resulting from the frictional force of the surface during turning), but also form-fittingly transmitted to the screw.

This has the advantage that the maximum transmittable torque from the screwdriving tool to the screw can be increased. Since the punch geometry is created, i.e. imprinted, by the screwdriving tool during assembly, the recess/imprint in the screw head corresponds exactly to the punch geometry/surface shape of the screwdriving tool. This has the effect that the torque is transmitted to the screw in a form-fitting manner, i.e. 'slip-free' or 'torque-loss-free', and the screw can be screwed into the internal thread with a lower torque applied by the screwdriving tool.

According to a preferred embodiment, the assembly method may comprise the following step:
  centered aligning of the screwdriving tool and the screw when the axial compression force is applied to the screw by the screwdriving tool.

The centered alignment can ensure suitable force transmission.

According to a preferred embodiment, the assembly method may comprise the following step:
  axially moving a tool shaft and a counterhold tool of the screwdriving tool for clamping the screw between its screw head and its screw shaft into the screwdriving tool, wherein the punch geometry is imprinted into the screwdriving tool by the clamping, and the screwdriving tool with the screw clamped therein is rotated relative to the instrument for screwing in the screw.

This means that according to the preferred embodiment of the assembly method, the screw can be clamped axially in the screwdriving tool during assembly, so that an axial pressure acting between the screwdriving tool and the screw can be increased while bypassing the internal thread (and avoiding an increased thread friction torque as a result).

In particular, the instrument may be configured such that a first branch of the two branches has a first through-hole and a second branch of the two branches has a second through-hole on which the internal thread is configured. According to a preferred embodiment, the assembly method may comprise the step of:

- axially moving the counterhold tool towards the tool shaft and through the second through-hole before clamping the screw into the screwdriving tool and inserting it into the internal thread, or
- passing the screw through the first through-hole and inserting the screw into the internal thread before moving the counterhold tool axially through the second through-hole towards the tool shaft and clamping the screw into the screwdriving tool.

Accordingly, the screw can first be clamped into the screwdriving tool before it is inserted and screwed into the internal thread, or the screw can first be inserted into the internal thread before it is clamped and screwed into the screwdriving tool.

Preferably, the screw can be secured in its screwed-in position, for example by laser welding and/or by adhesive, which can be applied before clamping in the screwdriving tool.

The object of the present disclosure is also solved by a screwdriving tool for performing a described assembly method, comprising a tool shaft having an end-side screw engagement portion which is provided and configured for transmitting torque to the screw and having an engagement surface from which a punch geometry protrudes which is provided and configured for imprinting the punch geometry into the screw upon transmission of an axial compression force toward the screw and transmitting torque from the punch geometry of the tool shaft in a form-fitting manner via the imprinted punch geometry to the screw.

According to a preferred embodiment, the engagement surface of the tool shaft may be concavely curved, in particular substantially spherical. Preferably, the engagement surface is smooth/unprofiled apart from the punch geometry. The engagement surface of the tool shaft may preferably be provided and configured in such a way that its shape corresponds substantially to the shape of the screw head. This means that the screw head preferably has a substantially convexly curved, in particular spherical surface (unprofiled apart from the imprinted punch geometry). This allows the tool shaft to be guided and centered in an advantageous manner. Thus, self-centering is preferably achieved during assembly or when applying the axial compression force from the screwdriving tool to the screw head.

According to a preferred embodiment, the punch geometry may have rounded edges. This has the advantage of avoiding the formation of sharp-edged crevices, slits, pockets or the like, since tissue residues, dirt and body fluids cannot be reliably and completely removed from these when the instrument is reprocessed. Another advantage of the rounded/soft-edged/curved surface design of the punch geometry is that damage can be avoided when the screwdriving tool slips off and thus any reworking of the screw, which is necessary to ensure the surface quality required for medical, in particular surgical, instruments/devices.

According to a preferred embodiment, the screwdriving tool may have a counterhold tool which is axially orientable or oriented with respect to the tool shaft and in opposition to the tool shaft such that its end-side screw engagement portion is axially opposed to the end-side screw engagement portion of the tool shaft and is provided and configured to transmit an axial compression force to the screw in the direction toward the tool shaft. In other words, in addition to the approximately punch-like tool shaft, the approximately punch-like counterhold tool may be provided having a common longitudinal axis and axially spaced from each other such that the screw engagement portion of the tool shaft faces the screw engagement portion of the counterhold tool. Thus, the screw can be arranged longitudinally aligned between the tool shaft and the counterhold tool. Furthermore, the counterhold tool is displaceable along its longitudinal axis towards the tool shaft, so that the compression force acting axially towards the tool shaft is transferable to the screw, and thus from the screw to the tool shaft. Consequently, a force acting between the screw engagement portion of the tool shaft and the screw corresponds to a sum of the compression force that can be applied by the tool shaft and the counterhold tool, respectively, in the direction of the opposite/opposed tool shaft or counterhold tool. The screw can thus be clamped axially between the tool shaft and the counterhold tool. This has the advantage that the axial pressure acting between the screwdriving tool and the screw can be increased while bypassing the internal thread (and avoiding an increased thread friction torque as a result). Simply put, the normal force on the surface of the screw, in particular the screw head, is increased, while the axial force acting on the screw (as a whole) in the direction of the counterhold tool remains the same or is compensated by the compression force of the counterhold tool.

According to a preferred embodiment, the punch geometry may have a form of a quality symbol, for example configured as a letter. Thus, the user can recognize that the assembly has been carried out with the method according to the application and that the screw has been tightened with a predetermined torque.

The present disclosure also relates to a screw kit comprising a described screwdriving tool and a screw having a screw head, the surface of which is preferably unprofiled and serves as an imprinting surface for imprinting the punch geometry. According to a preferred embodiment, the screw head may have a convex, preferably substantially spherical shape. In particular, the screw head may be configured as a body of revolution, i.e. as a rotationally symmetrical body that maps onto itself when rotated through any angle.

In other words, the assembly method according to the application can provide a connection element for surgical instruments that is optimized for cleaning and solves the problem of tissue residues, dirt and body fluids collecting and adhering in a slit of the screw or around the screw head, which are not completely removed during the reprocessing process. Disadvantages of previous connection elements include the fact that the sharp-edged slit base and gaps cannot be reliably cleaned, and that assembly errors that cannot be avoided in mass production, such as the slipping of a screwdriver, have to be reworked manually, for example by polishing. Thus, the object is to enable a combination of a design of a connection element head and a suitable assembly method in which there are no deep pockets, slits or the like with sharp edges at the bottom, but at the same time the holding forces of the secured connection are equal to or greater than before and the applied tightening torques/assembly forces can be finely adjusted/dosed. Here, the screw head and the thread end may be spherically shaped so that the spherical support guides the system and centers itself when the screw is clamped between its head and the thread end during the assembly process or when the screw-driving tool is pressed onto the screw with the axial compression force. During the clamping process, a defined geometry is imprinted in the contact point of the screw, which is used for form-fit and force-fit force transmission. During this process, the tightening torque or the action or the section modulus of the moving parts can be sensitively adjusted and/or measured and/or recorded via a sensor system. The screw connection can be secured in this screw position, if necessary, via adhesive, a laser welding spot or the like. Since the screw head is designed without a slit or similar element of force transmission (form-fitting means) prior to assembly, the connection element does not have to be reworked to achieve the surface quality required for surgical instruments/devices. In summary, this results in higher mechanical strength, process-reliable/reproducible machinability, simplification of assembly by increasing the degree of mechanization during manufacture, and better cleaning properties.

DETAILED DESCRIPTION

Preferred embodiments of the present disclosure are described below based on the accompanying Figures.

Figure 1:
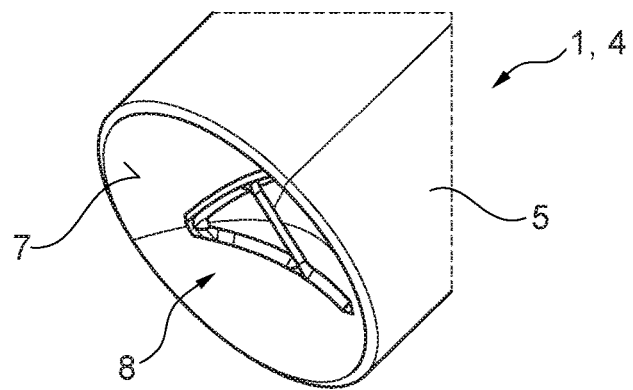
FIG. 1 shows a perspective view of a part of a screw-driving tool according to the application, which is provided for performing an assembly method according to the application.

FIG. 1 shows a perspective view of a section of a screwdriving tool 1 according to the application. The screwdriving tool 1 is used to screw a screw 2 with an external thread into an internal thread. The internal thread is configured on a surgical instrument 3 in the embodiment shown. In the embodiments shown, the screw 2 fixes two components of the instrument 3 so that they are movable, in particular pivotable, relative to each other.

The screwdriving tool 1 has a tool shaft 4 with an end-side screw engagement portion 5, which is provided and configured for transmitting a torque to the screw 2, in particular to a screw head 6 of the screw 2.

The screw engagement portion 5 of the tool shaft 4 has an engagement surface 7 from which a punch geometry 8 protrudes, which is provided and configured to imprint the punch geometry 8 into the screw 2 (to create an imprinted punch geometry 9) upon transmission of an axial compression force toward the screw 2 and to transmit torque from the punch geometry 8 of the tool shaft 4 (friction- and) form-fitting to the screw 2 via the imprinted punch geometry 9.

The engagement surface 7 may preferably correspond to a shape of the screw head 6 and may in particular be concavely curved. Preferably, the engagement surface 7 may be spherical (or spherical segment-shaped). Preferably, the engagement surface 7 is smooth/unprofiled apart from the punch geometry 8.

Preferably, the punch geometry 8 (and thus also the imprinted punch geometry 9) may have rounded edges. The punch geometry 8 may be in the form of a quality symbol, for example configured as a letter. In the embodiment shown, the punch geometry 8 has the shape of an 'A'.

Figure 2:
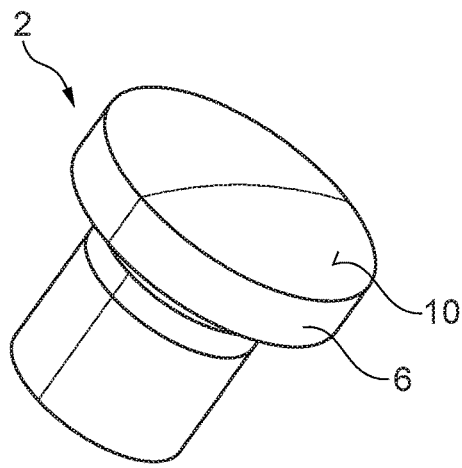
FIGS. 2 and 3 show perspective views of a screw that can be screwed in using the screwdriving tool before assembly and of an instrument into which the screw has been screwed using the assembly method according to the application.

FIG. 2 shows the screw 2, which can be screwed into the instrument 3 using the assembly method according to the application, before assembly. In particular, the screw head 6 may have an unprofiled, i.e. smooth, for example flat or curved, surface 10 without form-fitting engagement surfaces before assembly. The surface 10 serves as an imprinting surface for imprinting the punch geometry 8. In the illustrated embodiment, the screw head 6 is configured to be a body of revolution, i.e., a rotationally symmetric body that maps onto itself when rotated through any angle. In the illustrated embodiment, the surface 10 of the screw head 6 is convexly curved.

Figure 3:
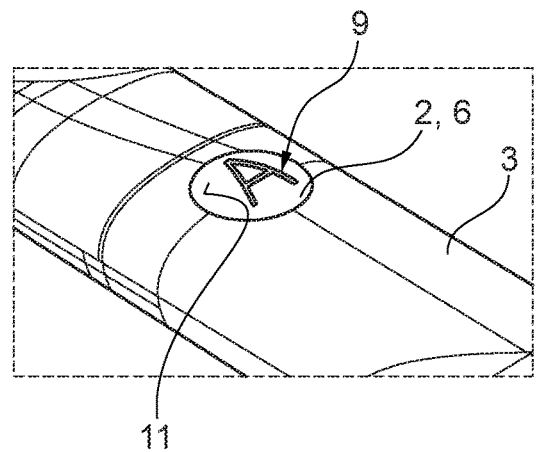

During assembly, the punch geometry 8 is imprinted into the screw head 6 (i.e. into the surface 10 of the screw head 6), so that after assembly (cf. FIG. 3) the screw head 6 has a profiled, i.e. relief-like, surface 11 in which a recess in the form of the punch geometry 8, i.e. the imprinted punch geometry 9, is configured, which can serve as a form-fitting engagement surface when screwing in. When the screwdriving tool 1 is rotated, the punch geometry 8 of the screwdriving tool 1 engages the imprinted punch geometry 9, so that the torque from the screwdriving tool 1 to the screw 2 can be transmitted not only frictionally engaged, but also in a form-fitting manner to the screw 2.

Figure 4:
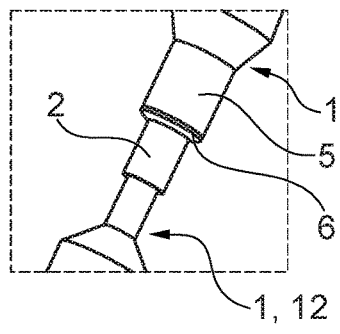
FIGS. 4 to 6 show further perspective views of the screwdriving tool at different times during the assembly method performed therewith.
Figure 5:
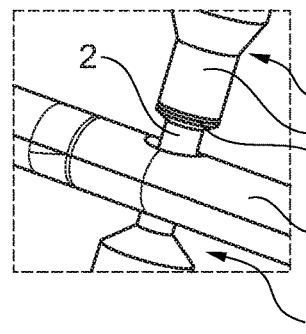
Figure 6:
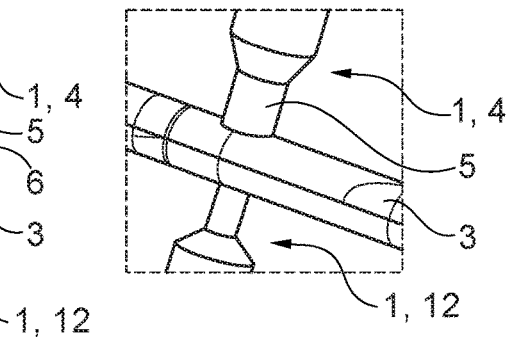

Preferably, the screwdriving tool 1 may have a counter-hold tool 12 that is axially orientable or oriented with respect to the tool shaft 4 and in the opposite direction to the tool shaft 4 such that its end-side screw engagement portion is axially opposite to the end-side screw engagement portion 5 of the tool shaft 4 and is provided and configured to transmit an axial compression force in the direction towards the tool shaft 4 to the screw 2 (cf. FIGS. 4 to 6). This allows the screw 2 to be clamped in the screwdriving tool 1 for imprinting the punch geometry 8 and for form-fitting and frictionally engaged transmission of the torque from the screwdriving tool 1 to the screw 2.

The present disclosure also relates to an assembly method for screwing the screw 2 into the internal thread of a medical instrument 3 to connect two branches 13 of the instrument 3 such that the two branches 13 are pivotable with respect to each other. The medical instrument 3 and a preferred embodiment is shown in more detail in FIG. 7 and will be described later.

In a step of the assembly method, the punch geometry 8 is imprinted into a preferably unprofiled screw head 6 (cf. FIG. 2) of the screw 6 by applying an axial compression force to the screw 2 using the screwdriving tool 1 itself. In this process, the surface 10 of the screw head 6, which was unprofiled before assembly, serves as an imprinting surface. In a subsequent step of the assembly method, the screwdriving tool 1 is rotated relative to the instrument 3 about a longitudinal screw axis in order to transmit a torque (in particular for setting a tightening torque or a screw-in depth of the screw) from the screwdriving tool 1 in a form-fitting manner via the imprinted punch geometry 9 to the screw 2 and to screw the screw 2 into the internal thread (see FIG. 3).

Preferably, the screwdriving tool 1 and the screw 2 can be arranged in a centered position when the axial compression force is applied to the screw 2 by the screwdriving tool 1. The centered alignment takes place in particular via the concave engagement surface 8 and the convex configured, unprofiled surface 10 of the screw head 6.

Preferably, the screwdriving tool has the counterhold tool 12 (cf. FIGS. 4 to 6). In particular, the tool shaft 4 and the counterhold tool 12 of the screwdriving tool 1 can be moved towards each other for clamping the screw 2 between its screw head 6 and its screw shaft in the screwdriving tool 1. In the process, the punch geometry 8 is imprinted into the screwdriving tool 1 by the clamping, and the screwdriving tool 1 is rotated relative to the instrument 3 with the screw 2 clamped therein for screwing in the screw 2.

In particular, the instrument 3 may be configured such that a first branch 13 of the two branches 13 has a first through-hole and a second branch 13 of the two branches 13 has a second through-hole on which the internal thread is configured. For example, the counterhold tool 12 may be moved towards the tool shaft 4 and through the second through-hole before the screw 2 is clamped into the screwdriving tool 1 as well as inserted into the internal thread. Alternatively, the screw 2 can be passed through the first through-hole and inserted into the internal thread before the counterhold tool 12 is moved axially through the second through-hole towards the tool shaft 4 and the screw 2 is clamped into the screwdriving tool 1.

Preferably, the screw 2 can be secured in its screwed-in position, for example by laser welding and/or by adhesive, which can be applied before clamping into the screwdriving tool 1.

Figure 7:
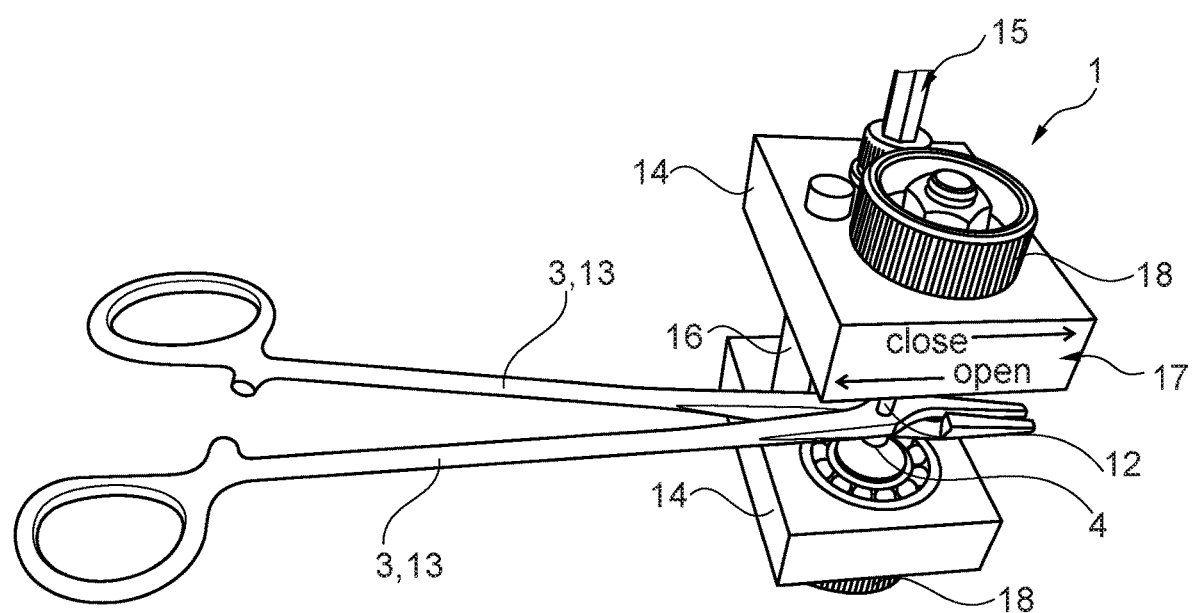
FIG. 7 shows a perspective view of a preferred embodiment of the screwdriving tool according to the application.

FIG. 7 shows the preferred embodiment of the screwdriving tool 1, in which the screwdriving tool 1 comprises the tool shaft 4 and the counterhold tool 12. In addition, FIG. 7 shows the branches 13 of the instrument 3, which are connected to each other by the assembly method according to the application via the screw 2 in such a way that the two branches 13 are pivotable to each other.

The screwdriving tool 1 may have a holder 14 to which the tool shaft 4 and/or the counterhold tool 12 are attached. In the embodiment shown, the holder 14 has a first receptacle on which the tool shaft 4 is rotatably mounted and a second receptacle on which the counterhold tool 12 is rotatably mounted.

The screwdriving tool 1 may additionally have a compression-force device 15. The compression-force device 15 is provided and configured to adjust, calculate and/or measure the compression force (from the counterhold tool 12 axially towards the tool shaft 4 on the screw 2 or from the tool shaft 4 axially towards the counterhold tool 12 on the screw 2). An axial distance between the two receptacles can be adjusted via the compression-force device 15. The holder 14 has an axial guide 16, in this case in the form of two rods aligned parallel to the axis of rotation, by which an adjustment of the axial distance parallel to the axis of rotation is guided. A scale 17 can be configured on the holder 14, which indicates the closing or opening direction of the screwdriving tool 1.

The screwdriving tool 1 may additionally have a tightening device 18, which is provided and configured to adjust and/or measure a rotation angle and/or the torque of the tool shaft 4 and/or counterhold tool 12. The tightening device 18 can be manually or preferably automatically actuated. The tightening device 18 can be configured in the form of a tightening wheel connected to the tool shaft 4 in a rotationally fixed manner or a tightening wheel connected to the counterhold tool 12 in a rotationally fixed manner.

The invention claimed is:

1. An assembly method for screwing a screw into an internal thread of a medical instrument in order to connect two branches of the medical instrument to each other such that the two branches are pivotable relative to each other, using a screwdriving tool, the assembly method comprising the steps of:
    imprinting a punch geometry into a screw head of the screw by applying an axial compression force to the screw using the screwdriving tool; and
    rotating the screwdriving tool relative to the medical instrument about a longitudinal screw axis to transmit torque from the screwdriving tool in a form-fitting manner via the punch geometry to the screw and to screw the screw into the internal thread.

2. The assembly method according to claim 1, further comprising the step of:
    aligning the screwdriving tool and the screw when the axial compression force is applied to the screw by the screwdriving tool.

3. The assembly method according to claim 1, wherein the screw head is unprofiled.

4. The assembly method according to claim 1 further comprising the step of:
    axially moving a tool shaft and a counterhold tool of the screwdriving tool for clamping the screw into the screwdriving tool, wherein the punch geometry is imprinted into the screwdriving tool when the screw is clamped into the screwdriving tool and the screwdriving tool and the screw are rotated relative to the medical instrument for screwing in the screw.

5. The assembly method according to claim 4, wherein a first branch of the two branches comprises a first through-hole and a second branch of the two branches comprises a second through-hole at which the internal thread is configured, and the method further comprises the step of:
    axially moving the counterhold tool towards the tool shaft and through the second through-hole before clamping the screw into the screwdriving tool and inserting the screw into the internal thread.

6. The assembly method according to claim 4, wherein a first branch of the two branches comprises a first through-hole and a second branch of the two branches comprises a second through-hole at which the internal thread is configured, and the method further comprises the step of:
    passing the screw through the first through-hole and inserting the screw into the internal thread before moving the counterhold tool axially through the second through-hole towards the tool shaft and clamping the screw into the screwdriving tool.

* * * * *